US00PP32176P3

(12) United States Plant Patent
Bean

(10) Patent No.: US PP32,176 P3
(45) Date of Patent: Sep. 8, 2020

(54) ***AGAPANTHUS* PLANT NAMED 'WP003'**

(50) Latin Name: ***Agapanthus* hybrid**
Varietal Denomination: WP003

(71) Applicant: Quinton Bean, Linbro Park (ZA)

(72) Inventor: Quinton Bean, Linbro Park (ZA)

( * ) Notice: Subject to any disclaimer, the term of this patent is extended or adjusted under 35 U.S.C. 154(b) by 0 days.

(21) Appl. No.: 16/501,854

(22) Filed: Jun. 19, 2019

(65) Prior Publication Data

US 2019/0394920 P1 Dec. 26, 2019

Related U.S. Application Data

(60) Provisional application No. 62/687,452, filed on Jun. 20, 2018.

(51) Int. Cl.
*A01H 5/02* (2018.01)
*A01H 6/04* (2018.01)

(52) U.S. Cl.
USPC ..... Plt./398
CPC ..... *A01H 6/04* (2018.05)

(58) Field of Classification Search
USPC ..... Plt./398
CPC ..... A01H 6/04
See application file for complete search history.

*Primary Examiner* — Anne Marie Grunberg
(74) *Attorney, Agent, or Firm* — Samuel R. McCoy, Jr.

(57) ABSTRACT

A new cultivar of *Agapanthus*, 'WP003', that is characterized by a medium plant size, inflorescences that form dense umbels of white flowers, an extended flowering season with blooming and re-blooming from early spring to late summer and sporadically in early fall, and a very floriferous blooming period producing an unusually high number of inflorescences.

2 Drawing Sheets

Latin name of the genus and species: The Latin name of the novel variety disclosed herein is *Agapanthus* hybrid.

Variety denomination: The inventive variety of *Agapanthus* hybrid disclosed herein has been given the variety denomination 'WP003'.

BACKGROUND OF THE INVENTION

Parentage: The cultivar 'WP003' is a seedling selection resulting from a controlled pollination breeding program by the Inventor in Hartebeespoort, Northwest Province, South Africa. The objective of the breeding program is to develop new cultivars of *Agapanthus* that are fast growing, early flowering and that display repeat flowering and unique flower colors. The inventor made a controlled cross in October of 2009 between an unnamed *Agapanthus* hybrid plant (not patented) from the Inventor's breeding program as the seed parent and an unnamed *Agapanthus* hybrid plant (not patented) from the Inventor's breeding program as the pollen parent. The inventor initially selected 'WP003' in November of 2010 as a single unique plant amongst the seedlings that resulted from the above cross. Upon confirmation of distinctness and stability, 'WP003' was selected for commercialization in November of 2011.

Asexual Reproduction: Asexual propagation of the new cultivar was first accomplished by division by the Inventor in Hartebeespoort, Northwest Province, South Africa in November of 2012. Asexual propagation by division and meristematic tissue culture through five successive generations has determined that the characteristics of the new cultivar are stable and are reproduced true to type in successive generations.

SUMMARY OF THE INVENTION

The following traits have been repeatedly observed and represent the characteristics of the new cultivar. The characteristics in combination distinguish 'WP003' as a distinct cultivar of *Agapanthus*.

1. 'WP003' exhibits a medium plant size.
2. 'WP003' exhibits inflorescences that form dense umbels of white flowers.
3. 'WP003' exhibits an extended flowering season blooming and re-blooming from early spring to late summer and sporadically in early fall.
4. 'WP003' exhibits a very floriferous blooming period producing an unusually high number of inflorescences.

DETAILED BOTANICAL DESCRIPTION OF THE VARIETY

Figure 1:
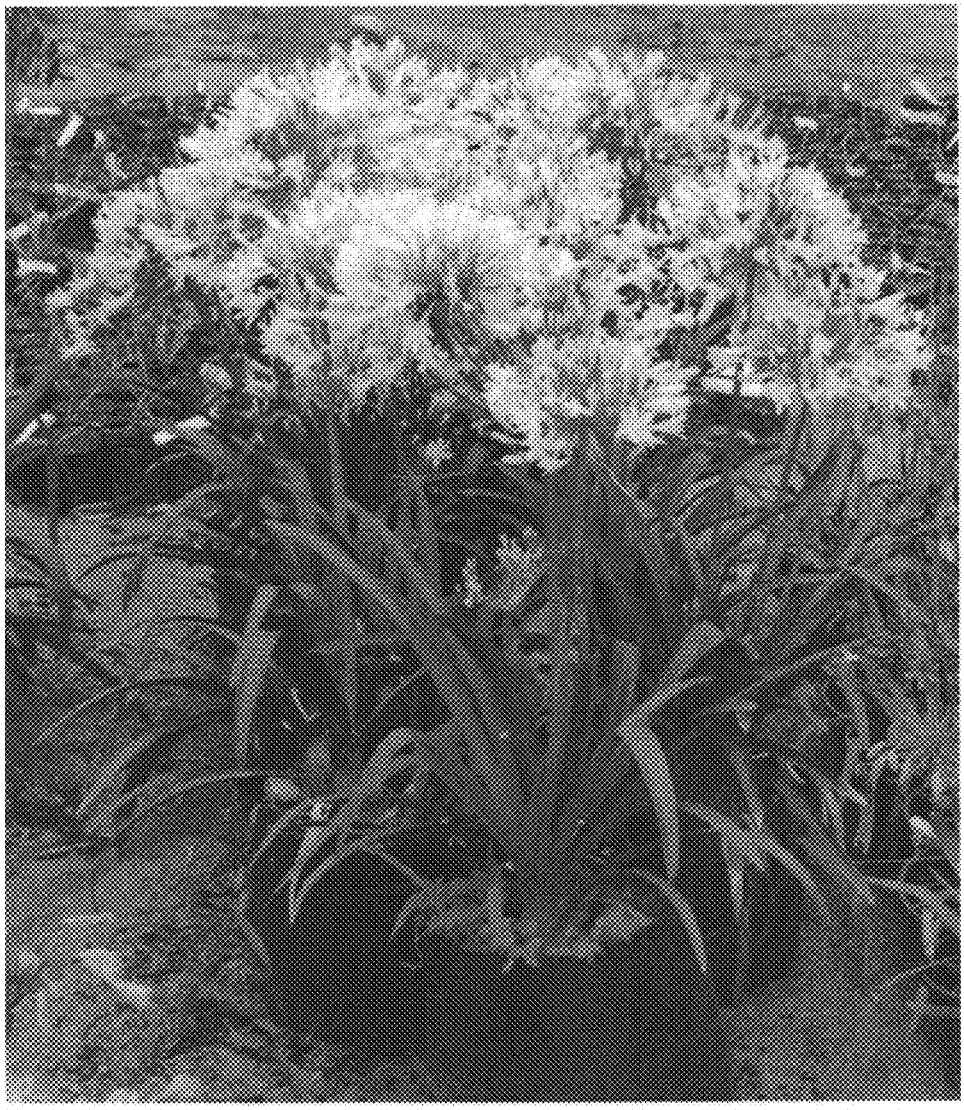
FIG. 1 shows as true as is reasonably possible to obtain in color photographs of this type, an exemplary 'WP003' specimen, approximately 24 months of age, grown at a wholesale nursery in Hartebeespoort, Northwest Province, South Africa under 40 percent shade.
Figure 2:
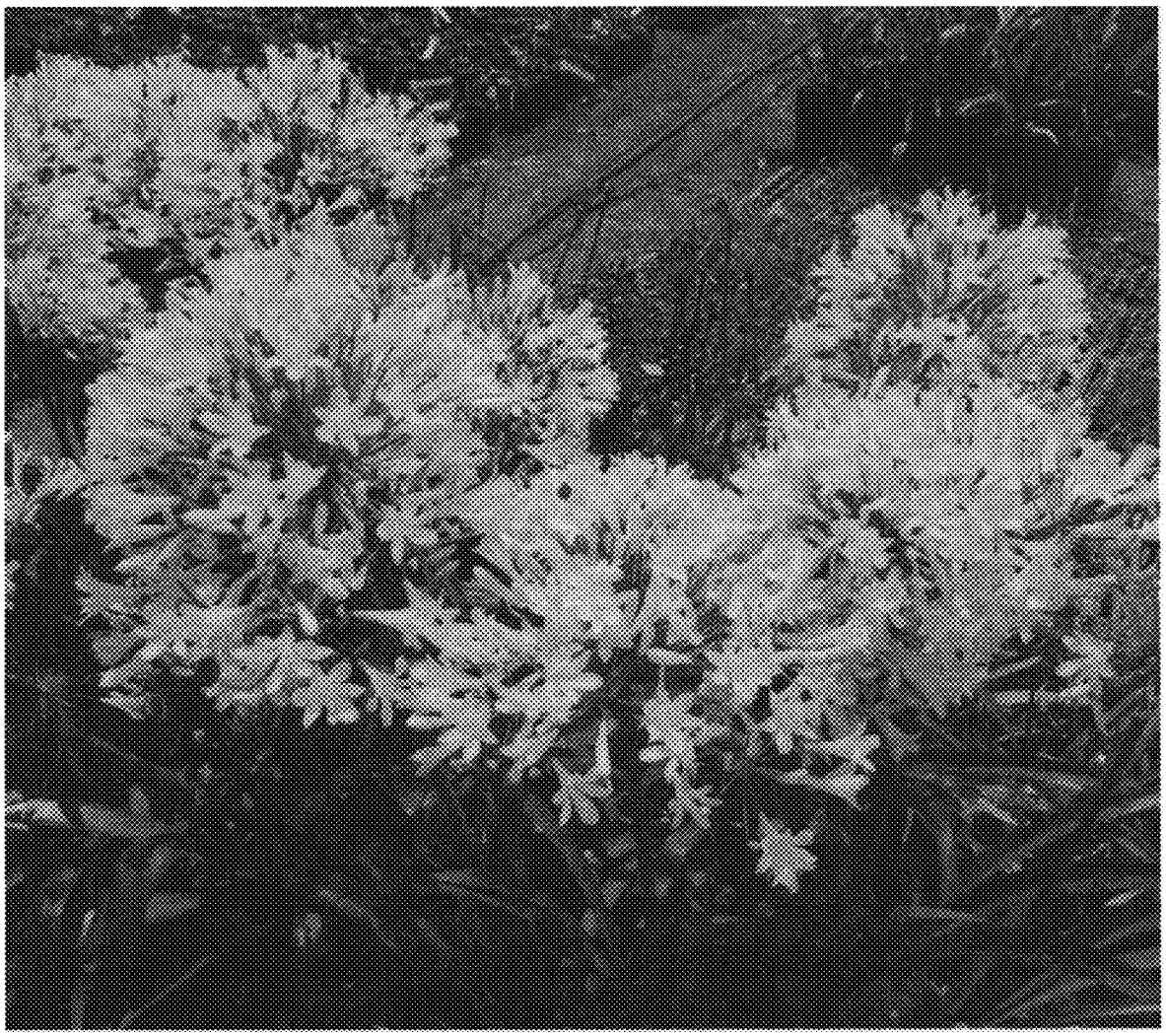
FIG. 2 shows as true as is reasonably possible to obtain in color photographs of this type, the exemplary umbel of 'WP003'.

The following observations and measurements made in January of 2018 and, unless otherwise indicated, describe a 24 month old 'WP003' plant which was grown outdoors in a 25 cm container in Clarendon, New South Wales, Australia. Plants were produced in full sun, using conventional production protocols for *Agapanthus* which consisted of regular overhead irrigation and controlled-release fertilizer applications. No chemical pest or disease measures were utilized in production.

Those skilled in the art will appreciate that certain characteristics will vary with older or, conversely, with younger plants. 'WP003' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'WP003' and comparisons with the parents and closest known commercial variety are provided below.

General plant description:

*Plant habit*.—Rhizomatous herbaceous perennial with an arching habit.

*Height*.—30 cm to the top of the foliar plane and 50 cm to the top of the floral plane.

*Width*.—45 cm.

*Hardiness*.—USDA Zones 9 through 11.

*Environmental tolerances*.—Prefers to be grown in filtered sun. Drought tolerant once established; moderate to good recovery with watering after severe wilting. Tolerates a wide range of soil types from sandy loam to loamy clay.

*Pest and disease susceptibility or resistance*.—'Plants have not been observed to be susceptible or resistant to pathogens and pests common to *Agapanthus*.

*Propagation*.—Propagation is accomplished through division of rhizomes and also meristematic tissue culture.

*Time to initiate roots*.—Approximately 3 weeks.

*Crop time*.—Depending on latitude of and microclimate of growing location, a fully rooted cutting requires approximately 3 months with an additional 6 to 9 months needed to produce a mature and marketable 25 cm container.

Roots: The roots are fibrous and freely-branched, colored white, fleshy, similar to other *Agapanthus*; high root density.

Stem:

*Branching habit*.—Acaulescent, rhizomatous plant with shoots emerging from rhizomes with an upright attitude.

Basal shoots:

*Shoots density*.—4 divisions, or propagules, per nursery pot, with the oldest propagules near the center of the plant's crown possessing 14 to 16 leaves and shoots of varying ages and sizes.

*Shoot strength*.—Medium.

*Cross section*.—Concave.

*Shoot color, adaxial surface*.—Nearest to yellow-green, a mixture of RHS 144A and 144B.

*Shoot color, abaxial surface*.—Yellow-green, RHS 144B.

*Shoot surface texture*.—Smooth.

Foliage:

*Arrangement*.—Alternate.

*Division*.—Simple.

*Attachment*.—Acaulescent.

*Mature leaf dimensions*.—40 cm long, 2.5 cm wide at the widest point and 0.2 cm thick.

*Attitude*.—Arched.

*Shape*.—Linear.

*Apex*.—Acute.

*Base*.—Sheathed.

*Cross section*.—Flat.

*Margins*.—Entire.

*Texture and luster, adaxial surface*.—Smooth and glossy.

*Texture and luster, abaxial surface*.—Smooth and glossy.

*Pubescence, adaxial surface*.—Glabrous.

*Pubescence, abaxial surface*.—Glabrous.

*Color*.—Juvenile foliage, adaxial surfaces — Green, RHS 137A. Juvenile foliage, abaxial surfaces — Green, RHS 137C. Mature foliage, adaxial surfaces — Green, RHS 137A. Mature foliage, abaxial surfaces — Green, RHS 137C.

*Venation*.—Type — Parallel. Color, adaxial surfaces — Green, RHS 137A. Color, abaxial surfaces — Green, RHS 137C.

*Petiole*.—Leaves are acaulescent; sessile.

*Stipules*.—Absent.

Inflorescence:

*Bloom habit*.—Recurrent.

*Bloom period*.—Early spring to late summer and sporadically in early fall.

*Inflorescence type*.—Umbellate.

*Umbel diameter*.—Approximately 13 cm wide and 8 cm tall.

*Number of inflorescences per pot*.—Up to 4 flowering scapes per plant.

*Number of flowers per umbel*.—Approximately 50.

*Scape*.—Length — 60 cm. Width — Elliptical; 0.9 cm by 0.8 cm. Texture — Smooth; glabrous. Color — Green, RHS 138A. Strength — Strong.

Buds:

*Bud shape*.—Oblanceolate.

*Bud dimensions*.—26 mm long and 6 mm wide.

*Bud color*.—White, RHS 155A.

*Bud texture*.—Glabrous.

Flowers:

*Shape*.—Funnelform.

*Arrangement*.—Rotate.

*Persistence*.—Non-persistent.

*Lastingness*.—One to two days.

*Aspect*.—Upward and outward.

*Fragrance*.—Non-fragrant.

*Pedicels*.—Dimensions — 4.0 cm long and 0.2 cm in diameter. Attitude — Erect to semi-erect. Texture — Smooth. Color — Green, RHS 138A. Strength — Strong.

*Perianth*.—General description — Perianth is comprised of six tepals, arranged in a single whorl. Dimensions — Approximately 14 mm in diameter and 26 mm deep, from the base of the receptacle.

*Tepals*.—Quantity — Six basally fused tepals. Shape — Oblanceolate. Apex — Obtuse. Base — Fused. Aspect — Concave. Dimensions, free portion of tepals — 15 mm long and 6.75 mm wide, as measured. Texture — Smooth; glabrous. Margin — Entire. Color, when opening — Outer tepal — White, RHS 155C. Inner tepal — White, RHS 155A. Color, when fully open — Outer tepal — White, RHS 155C. Inner tepal — White, RHS 155A.

Reproductive organs:

*Stamens*.—Quantity — Six. Attachment — Each is adnate to a corresponding tepal.

*Filament*.—Color — White, RHS NN155B. Dimensions — 23 mm long and approximately 0.6 mm wide. Attachment — Dorsifixed.

*Anther*.—Shape — Oblong. Dimensions — 1.85 mm long and 0.6 mm wide. Color — Orange-yellow, RHS 163B.

*Pollen*.—Abundance — Moderately abundant. Color — Orange-yellow, RHS 163D.

*Pistil*.—Quantity — One. Dimensions — 18 mm long, from apex of ovary; width is approximately 0.3 mm. Color — Violet-Blue RHS 92D at base, becoming Violet-Blue RHS 92C near apex.

*Stigma*.—Shape — Compact, punctiform. Color — Yellow-Green RHS 145C. Diameter — 3 mm. Color — White, RHS NN155D.

*Style*.—Shape — Filiform. Dimensions — 18 mm long and 0.03 mm wide. Color — White, RHS NN155D.

*Ovary*.—Shape — Oblong. Color — Yellow-Green RHS 145C. Dimensions — 8 mm long and 2 mm wide. Position — Superior.

Fruit and seeds: Not observed.

COMPARISONS WITH THE PARENT PLANTS

The new *Agapanthus* plant 'WP003' may be distinguished from the seed parent, an unnamed *Agapanthus* hybrid plant (not patented), by the following combination of characteristics described in Table 1 below.

TABLE 1

| Characteristic | 'WP003' | Unnamed seed parent. |
|---|---|---|
| Foliage length. | Shorter than the parent. | Longer than 'WP003'. |
| Height of inflorescence. | Shorter than the parent. | Taller than 'WP003'. |
| Floriferousness. | More floriferous. | Less floriferous. |
| Quantity of flowers per umbel. | More flowers per umbel. | Fewer flowers per umbel. |

The new *Agapanthus* plant 'WP003' may be distinguished from the pollen parent, an unnamed *Agapanthus* hybrid plant (not patented), by the following combination of characteristics described in Table 2 below.

TABLE 2

| Characteristic | 'WP003' | Unnamed pollen parent. |
|---|---|---|
| Foliage length. | Shorter than the parent. | Longer than 'WP003'. |
| Height of inflorescence. | Shorter than the parent. | Significantly taller than 'WP003'. |
| Floriferousness. | More floriferous. | Less floriferous. |
| Quantity of flowers per umbel. | Fewer flowers per umbel. | More flowers per umbel. |

COMPARISONS WITH THE MOST SIMILAR *AGAPANTHUS* CULTIVAR KNOWN TO THE INVENTOR

The new *Agapanthus* plant 'WP003' may be distinguished from the most similar variety known to the breeder, *Agapanthus* 'White Ice' (not patented), by the following combination of characteristics described in Table 3.

TABLE 3

| Characteristic | 'WP003' | 'White Ice' |
|---|---|---|
| Bloom habit. | Good reblooming. | Poor reblooming. |
| Floriferousness. | More floriferous. | Less floriferous. |
| Quantity of flowers per umbel. | More flowers per umbel. | Fewer flowers per umbel. |

That which is claimed is:

1. A new and distinct *Agapanthus* hybrid plant selection named 'WP003', substantially as described and illustrated herein.

* * * * *